United States Patent [19]

Debernard et al.

[11] Patent Number: 5,747,303
[45] Date of Patent: May 5, 1998

[54] INTERMEDIATES OF PEPTIDE ANTAGONISTS OF NEUROTENSIN

[75] Inventors: Jean-Jacques Debernard, Marolles En Brie; Catherine Dubertret, Sevres; Gérard Helynck, Choisy Le Roi; Jean Leboul, Gometz La Ville; Jean-Paul Martin, Colombes, all of France

[73] Assignee: Rhone-Poulenc Rorer S.A., Antony Cedex, France

[21] Appl. No.: 737,697

[22] PCT Filed: May 17, 1995

[86] PCT No.: PCT/FR95/00642

§ 371 Date: Nov. 19, 1996

§ 102(e) Date: Nov. 19, 1996

[87] PCT Pub. No.: WO95/32217

PCT Pub. Date: Nov. 30, 1995

[30] Foreign Application Priority Data

May 20, 1994 [FR] France ................... 94 06166

[51] Int. Cl.⁶ ............... C07D 267/22; C07D 245/04
[52] U.S. Cl. ............ 435/119; 435/120; 435/127; 530/338; 540/456; 540/460; 540/461; 540/472; 549/200
[58] Field of Search .................. 530/330, 317, 530/338; 435/117, 119, 120, 127; 540/456, 460, 461, 472; 549/200

[56] References Cited

U.S. PATENT DOCUMENTS 5,162,497 11/1992 Coy et al. .................. 530/314
5,430,047 7/1995 Johnson et al. ............ 514/381

OTHER PUBLICATIONS

Brown, A.G. and P.D. Edwards, 1990, Tetrahedron Letters, vol. 31, No. 45, pp. 6581–6584, 1990.
Ser. No. 08/737695, F.–F. Clerc et al., pp. 1–40.
J. H. Walsdorff (ED.), Cittilin, Report of Scientific Results 1991, p. 68.

W. Trowitzsch–Kienest et al., Cittilins: Bicyclic Isotrityrosines from Myxococcus xanthus, German Chemists' Society, 24th General meeting, Sep. 5–11, 1993, pp. 496–497.
F. Rioux et al., Pharmacological characterization of Neurotensin Receptors in the Rat Isolated Portal Vein Using Analogues and Fragments of Neurotensin, European Journal of Pharmacology, 66, 1980, pp. 273–279.
L. A. Miller et al., Inhibitory effects of the neurotensin8–13 analogs Asp13–NT8–13 and Asp12–NT8–13 on mast cell secretion, Agents Actions, 38, 1993, pp. 1–7.
C. Granier et al., Synthesis and Characterization of Neurotensin Analogues for Structure/Activity Relationship Studies, Eur. J. Biochem., 124, 1982, pp. 117–125.
A. G. Brown et al., Synthesis of Analogues of the Biphenomycin Antibiotics, Tetrahedron Letters, 31(45), 1990, pp. 6581–6584.

*Primary Examiner*—James Ketter
*Assistant Examiner*—Irem Yucel
*Attorney, Agent, or Firm*—Raymond S. Parker, III; Michael B. Martin; Martin F. Savitzky

[57] ABSTRACT

The invention is directed to a novel compound of formula

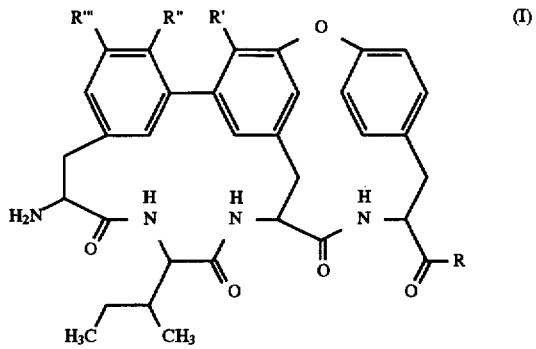

in which R is a hydroxyl, alkyloxy, phenylalkyloxy or —NH—CH$_2$—COOH radical, R' and R" are identical and are each a hydroxy or methoxy radical and R'" represents a hydrogen, bromine, chlorine or iodine atom or a nitro radical. The invention is also directed to the salts of said compounds and their use.

10 Claims, No Drawings

INTERMEDIATES OF PEPTIDE ANTAGONISTS OF NEUROTENSIN

The present invention relates to new compounds of formula:

(I)

to their salts, to their preparation and to their use.

In the formula (I), R represents a hydroxyl, alkyloxy, phenylalkyloxy or —NH—CH$_2$—COOH radical, R' and R" are identical and each represent a hydroxyl or methoxy radical and R'" represents a hydrogen, bromine, chlorine or iodine atom or a nitro radical.

In the preceding and following definitions, the alkyl and alkyloxy radicals and portions contain 1 to 4 carbon atoms in a straight or branched chain, Arg means arginine, Lys means lysine, Pro means proline, Fmoc means 9-fluorenylmethoxycarbonyl, Pmc means 2,2,5,7,8-pentamethylchroman-6-sulphonyl and Boc means tert-butoxycarbonyl.

The compound of formula (I) in which R, R' and R" represent a hydroxyl radical and R'" represents a hydrogen atom can be prepared by fermentation of A9738 actinomycetes (CBS 162.94) and isolation of the product.

The fermentation is carried out according to conventional fermentation processes. A medium comprising peptone, a yeast extract, a meat extract, glucose, calcium carbonate, sodium chloride and agar is preferably used as culture medium. This fermentation is preferably carried out at a temperature of between 25° and 30° C. The broth is then extracted and the aqueous phase ultrafiltered and chromatographed a number of times.

The compounds of formula (I) in which R represents an alkyloxy or phenylalkyloxy radical can be prepared by esterification of a corresponding compound of formula (I) in which R represents a hydroxyl radical.

This esterification is preferably carried out by reaction of an alcohol R—OH, in which R represents an alkyl or phenylalkyl radical, either in the presence of thionyl chloride, according to the method described by M. E. Jung et al., Tetrahedron Letters, 30(32), 4211–4 (1989), or in the presence of sulphuric acid or gaseous hydrochloric acid, at a temperature of between 0° and 25° C., or when R represents a benzyloxy radical, in the presence of para-toluenesulphonic acid, according to the method described by T. E. Walker et al., J. Org. Chem., 51, 1175–9 (1986). The tert-butyl ester can also be obtained by reaction with isobutene according to the process described in U.S. Pat. No. 3,496,219.

The compounds of formula (I) in which R represents an —NH—CH$_2$—COOH radical can be prepared by reaction with glycine of a corresponding compound of formula (I) in which R represents a hydroxyl radical.

It is particularly advantageous to use the compound of formula (I) in the activated form. Mention may be made, as activated form, of the reaction product of the compound of formula (I) with N-hydroxysuccinimide, N-hydroxybenzotriazole or 2-[1 H-benzotriazol-1-yl]-1,1,3,3-tetramethyluronium hexafluoromethylphosphate, which can be prepared in an inert solvent, such as an amide such as dimethylformamide or N-methyl-2-pyrrolidone, a chlorinated solvent such as chloroform or methylene chloride, an ether such as tetrahydrofuran or a mixture of these solvents, at a temperature of between 15° and 60° C., in the presence of 4 Å molecular sieve or of a coupling agent such as dicyclohexylcarbodiimide or alternatively a pentafluorophenyl ester which can be prepared according to the method described by L. Kisfaludy et al., Synthesis, 325–327 (1983).

The condensation is generally carried out under the same temperature and reaction mixture conditions as those described above for the preparation of the activated form of the compound of formula (I), optionally in the presence of pyridine or of an amine such as diisopropylethylamine. These reactions can be carried out without isolating the activated product.

The compounds of formula (I) in which R' and R" represent methoxy radicals can be prepared by reaction with trimethylsilyldiazomethane of a corresponding compound of formula (I) in which R' and R" represent hydroxyl radicals. When R represents an unprotected hydroxyl radical, a compound of formula (I) is obtained in which R, R' and R" are methoxy radicals.

This reaction is carried out in a lower aliphatic alcohol (methanol or ethanol, for example) at a temperature in the region of 20° C.

The compounds of formula (I) in which R'" represents a nitro radical can be prepared by nitration of a corresponding compound of formula (I) in which R'" represents a hydrogen atom.

This nitration is carried out by any known nitration method. Preferably, nitric acid is reacted, in acetic acid, at a temperature in the region of 20° C.

The compounds of formula (I) in which R'" represents a chlorine atom can be prepared by chlorination of a corresponding compound of formula (I) in which R'" represents a hydrogen atom.

This reaction is carried out by any known chlorination method. Preferably, 2,3,4,5,6,6-hexachloro-2,4-cyclohexadiene-1-one is reacted, in a dimethylformamide/carbon tetrachloride mixture, at a temperature in the region of 20° C., according to the method described by M. Lemaire et al., Janssen Chimica Acta, 5(1), 3–8 (1987).

The compounds of formula (I) in which R'" represents a bromine atom can be prepared by bromination of a corresponding compound of formula (I) in which R'" represents a hydrogen atom.

This reaction is carried out by any known bromination method. Preferably, bromine is reacted, in the presence of sodium acetate, in acetic acid, at a temperature in the region of 20° C.

The compounds of formula (I) in which R'" represents an iodine atom can be prepared by iodination of a corresponding compound of formula (I) in which R'" represents a hydrogen atom.

This reaction is carried out by any known iodination method. Preferably, an alkali metal iodide (sodium iodide or potassium iodide, for example) is reacted, in the presence of a reagent such as 1,2,4,6-tetrachloro-3α,6α-diphenylglycouril, in a low aliphatic alcohol such as methanol, at a temperature in the region of 20° C.

The compounds of formula (I) in which R represents a hydroxyl radical can optionally be converted to metal salts or to addition salts with nitrogenous bases according to methods known per se. These salts can be obtained by reaction, in a solvent, of a compound of formula (I) with a metal base (alkali metal or alkaline-earth metal, for example), ammonia, an amine or a salt of an organic acid. The salt formed is separated by the usual methods.

The compounds of formula (I) can optionally be converted to addition salts with an inorganic or organic acid by reaction with such an acid in an organic solvent, such as an alcohol, a ketone, an ether or a chlorinated solvent.

Mention may be made, as examples of salts, of the addition salts with inorganic or organic acids (such as acetate, trifluoroacetate, propionate, succinate, benzoate, fumarate, maleate, oxalate, methanesulphonate, isethionate, theophyllinacetate, salicylate, methylenebis-β-oxynaphthoate, hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, piperidine, benzylamine, N-benzyl-α-phenethylamine, choline, arginine, leucine, lysine or N-methylglucamine).

The compounds of formula (I) are particularly advantageous as intermediates in the preparation of active compounds as neurotensin antagonists of formula:

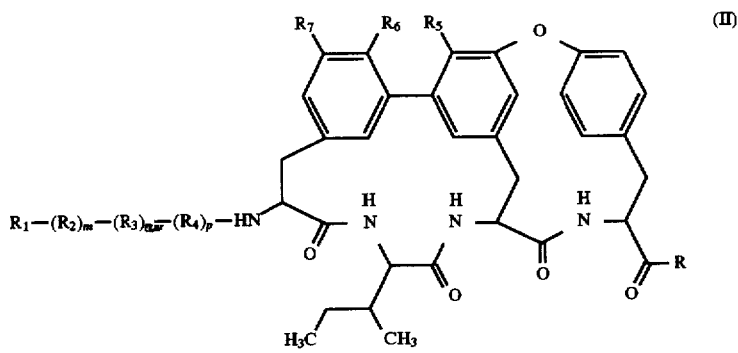

in which R represents a hydroxyl, alkyloxy, phenylalkyloxy or —NH—CH$_2$—COOH radical, R$_1$ represents a hydrogen atom, an adamantylacetyl, adamantylcarbonyl, norbornylacetyl, norbornylphenoxycarbonyl, benzoyl, nicotinoyl, 4-phenylbenzoyl, 4-tert-butylbenzoyl or 2-pyrrolidinecarbonyl radical or a protective group for an amine functional group, R$_2$ represents an Arg or Lys residue, R$_3$ represents an Arg or Lys residue, R$_4$ represents a Pro residue, m, n and p, which are identical or different, represent a number equal to 0 or 1, it being understood that, when R$_1$ represents a hydrogen atom, the sum m+n+p is at least equal to 1, R$_5$ and R6 are identical and represent a hydroxyl or methoxy radical and R$_7$ represents a hydrogen, chlorine, bromine or iodine atom or a nitro radical, and their equivalents in which the peptide bonds (CO—NH) between two amino acid residues are replaced by —CH$_2$—NH— bonds and/or the peptide bond (CO—NH) between the R$_2$ and R$_3$ amino acid residues is replaced by a —CH=CH— bond.

In the formula (II), each amino acid residue can be in the L or D configuration.

Mention may be made, as protective group for the amine functional group, of the 9-fluorenylmethoxycarbonyl, tert-butylcarbonyl, acetyl, pivaloyl and benzyloxycarbonyl groups, the phenyl in the benzyloxycarbonyl group being optionally substituted by halogen, alkyl, alkyloxy or nitro.

The peptide compounds of formula (II) in which the sum m+n+p is at least equal to 1 can be prepared by reaction of a compound of formula (I) with a derivative of formula:

R$_1$—(R$_2$)$_m$—(R$_3$)$_n$—(R$_4$)$_p$—OH (III)

in which R$_1$ represents an adamantylacetyl, adamantylcarbonyl, norbornylacetyl, norbornylphenoxycarbonyl, benzoyl, nicotinoyl, 4-phenylbenzoyl, 4-tert-butylbenzoyl or 2-pyrrolidinecarbonyl radical or a protective group for an amine functional group, R$_2$, R$_3$, R$_4$, n, m and p have the same meanings as in the formula (II) and the sum m+n+p is at least equal to 1, optionally followed by deprotection of the end amine functional group in order to obtain the compounds in which R1 represents a hydrogen atom and/or optionally, when R represents an alkyloxy or phenylalkyloxy radical, by deprotection of the carboxyl functional group in order to obtain the compounds in which R represents a hydroxyl radical.

Coupling of the derivatives of formulae (I) and (III) is carried out by any method known to a person skilled in the art for coupling an amino derivative and a peptide.

It is particularly advantageous to use the derivative of formula (III) in the activated form. Mention may be made, as activated form, of the reaction product of the derivative of formula (III) with N-hydroxysuccinimide, N-hydroxybenzotriazole or 2-[1 H-benzotriazol-1-yl]-1,1,3,3-tetramethyluronium hexafluoromethylphosphate, which can be prepared in an inert solvent, such as an amide such as dimethylformamide or N-methyl-2-pyrrolidone, a chlorinated solvent such as chloroform or methylene chloride, an ether such as tetrahydrofuran or a mixture of these solvents, at a temperature of between 15° and 60° C., in the presence of 4A molecular sieve or of a coupling agent such as dicyclohexylcarbodiimide or alternatively a pentafluorophenyl ester which can be prepared according to the method described by L. Kisfaludy et al., Synthesis, 325–327 (1983).

The condensation of the product of formula (I) with the activated product of formula (III) is generally carried out under the same temperature and reaction mixture conditions as those described above for the preparation of the activated form of the derivative of formula (III), optionally in the presence of pyridine or of an amine such as diisopropylethylamine. These reactions can be carried out without isolating the activated product.

It can be advantageous to carry out this reaction in the solid phase, on a resin. The preferred resins are 4-hydroxymethylphenoxy-methyl/styrene-1% divinylbenzene copolymer (HMP, Applied Biosystems, Wang, J. Amer. Chem. Soc., 95, 1328, (1973)) or chlorotrityl chloride/polystyrene-1% divinylbenzene copolymer (Novabiochem) resins.

The optional deprotection of the end amine functional group can be carried out according to the usual techniques for the deprotection of amines, such as those described by T. W. Greene, Protective Groups in Organic Synthesis, John Wiley, New York. It is possible, for example, to carry out the deprotection in an inert solvent such as dimethylformamide or a chlorinated solvent such as dichloromethane, in the presence of piperidine, at a temperature in the region of 20°–250° C.

The optional deprotection of the carboxyl functional group can be carried out by any method known to a person skilled in the art which makes it possible to change from a carboxylic ester functional group to a carboxyl functional group. Preferably, the deprotection is carried out in an inert solvent, such as dioxane, water or a mixture of these solvents, in the presence of lithium hydroxide, at a temperature in the region of 0° C.

The derivatives of formula (III) are marketed or can be prepared by application or adaptation of the methods described by S. Doulut et al., Peptide Research, 5(1), 30–38 (1992; J. Couder et al., Int. J. Peptide Res., 41, 181–184 (1993); V. K. Skukla et al., Can. J. Physiol. Pharmacol., 71, 211–216 (1993); M. H. Michael et al., J. Chem. Soc. Perkin I, 307–314 (1982); T. E. Christos et al., Bioorganic Medicinal Chemistry Letters, 3(6), 1035–1040 (1993), in Patents WO 93/00359 and WO 91/02750 and in the examples.

The compounds of formula (II) in which the sum m+n+p is at least equal to 1 and $R_1$ represents a hydrogen atom or a protective group for an amine functional group can also be prepared by reaction of the corresponding derivative of formula (I) with successively an $(R_4)_p$—OH and/or $(R_3)_n$—OH and/or $(R_2)_m$—OH derivative in which $R_4$, $R_3$ and $R_2$ have the same meanings as in the formula (I), the amino residues of which are preferably protected, optionally followed by deprotection.

This reaction is carried out under the conditions described in the literature for the chemistry of peptides, such as those described above for the coupling of the derivatives of formula (I) and formula (III).

The compounds of formula (II) in which the sum m+n+p is equal to zero and $R_1$ represents a protective group for the amine functional group can be prepared by any method known to a person skilled in the art for the protection of an amine functional group which does not modify the remainder of the molecule. In particular, when $R_1$ represents a 9-fluorenylmethoxycarbonyl radical, a compound of formula (I) is reacted with 9-fluorenylmethyl N-succinyl carbonate.

This reaction is generally carried out in an inert solvent, such as dioxane, in the presence of an aqueous sodium carbonate solution, at a temperature in the region of 20° C.

When $R_1$ represents a tert-butoxycarbonyl, acetyl, pivaloyl or benzyloxycarbonyl radical in which the phenyl is optionally substituted by halogen, alkyl, alkyloxy or nitro, a compound of formula (I) is reacted with a derivative $R_1$—Cl in which $R_1$ represents a tert-butoxycarbonyl, acetyl, pivaloyl or benzyloxycarbonyl radical in which the phenyl is optionally substituted by halogen, alkyl, alkyloxy or nitro.

This reaction is preferably carried out in an inert solvent, such as dimethylformamide, in the presence of a base, such as a trialkylamine (diisopropylethylamine, for example), at a temperature in the region of 20° C.

The compounds of formula (II) in which m+n+p is equal to zero and $R_1$ represents an adamantylacetyl, adamantylcarbonyl, norbornylacetyl, norbornylphenoxycarbonyl, benzoyl, nicotinoyl, 4-phenylbenzoyl, 4-tert-butylbenzoyl or 2-pyrrolidinecarbonyl radical can be prepared by reaction of a compound of formula (I) with a chloride $R_1$—Cl in which $R_1$ represents an adamantylacetyl, adamantylcarbonyl, norbornylacetyl, norbornylphenoxycarbonyl, benzoyl, nicotinoyl, 4-phenylbenzoyl, 4-tert-butylbenzoyl or 2-pyrrolidinecarbonyl radical.

This reaction is preferably carried out in an inert solvent, such as dimethylformamide, in the presence of a base, such as a trialkylamine (diisopropylethylamine, for example), at a temperature in the region of 20° C.

The compounds of formula (II) can be purified by the usual known methods, for example by chromatography or extraction.

It is understood by a person skilled in the art that, for the implementation of the processes described above, it may be necessary to introduce protective groups for the amino functional groups in order to avoid side reactions, such as those groups described by T. W. Greene, Protective Groups in Organic Synthesis, John Wiley, New York.

The compounds of formula (II) in which R represents a hydroxyl radical can optionally be converted to metal salts or to addition salts with nitrogenous bases according to methods known per se. These salts can be obtained by reaction, in a solvent, of a compound of formula (II) with a metal base (alkali metal or alkaline-earth metal, for example), ammonia, an amine or a salt of an organic acid. The salt formed is separated by the usual methods.

The compounds of formula (II) can optionally be converted to addition salts with an inorganic or organic acid by reaction with such an acid in an organic solvent, such as an alcohol, a ketone, an ether or a chlorinated solvent.

Mention may be made, as examples of pharmaceutically acceptable salts, of the addition salts with inorganic or organic acids (such as acetate, trifluoroacetate, propionate, succinate, benzoate, fumarate, maleate, oxalate, methanesulphonate, isethionate, theophyllinacetate, salicylate, methylenebis-β-oxynaphthoate, hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, piperidine, benzylamine, N-benzyl-oxphenethylamine, choline, arginine, leucine, lysine or N-methylglucamine).

The compounds of formula (II) have advantageous pharmacological properties. These compounds are antagonists of neurotensin and are therefore useful in treating or preventing disorders associated with neurotensin.

Thus it is that these compounds can be used for the treatment or prevention of psychoses, anxious disorders, depression, cognitive disorders, neurodegeneration, panic attacks, Parkinson's disease, Alzheimer's disease, schizophrenia, autism, tardive dyskinesia, irritable bowel syndrome, acute pancreatitis, ulcers, disorders of intestinal motility, certain tumours sensitive to neurotensin, in weaning from chronic treatments and alcohol or drug abuse, allergic and inflammatory phenomena, cardiovascular and respiratory disorders and asthma.

The affinity of the compounds of formula (II) with respect to neurotensin was measured by their ability to displace the binding of tritiated neurotensin of its receptors present in a crude guinea pig cerebral cortex membrane preparation. The test is based on that described by M. Goedert et al., Brain Research, 304, 71–81 (1984): male Dunkin-Hartley guinea pigs (200–300 g) are sacrificed by decapitation and the brain quickly removed. All the following stages are carried out at 4° C. The cerebral cortex is dissected, weighed and homogenized in 5 ml of Tris-HCl buffer (50 mM, pH 7.4) per gram of tissue with a polytron (force 6 for 15 seconds). The homogenate is centrifuged at 48,000 g for 15 minutes and the pellet obtained washed twice in the same buffer. The final pellet is homogenized in 3 ml of buffer per gram of starting tissue and retained in the form of aliquots (approximately 20 mg of proteins per ml) at −80° C. until use. The protein content is measured according to the method of Bradford, Anal. Biochem., 72, 248–254 (1976). The binding test is carried out in Tris-HCl 50 mM pH 7.4 buffer containing 0.4 % of bovine serum albumin and 0.1 mM of bacitracin in the presence of 0.15 mg of proteins per ml and 0.8 nM of [$^3$H]neurotensin for 15 minutes at 25° C. The non-specific binding is determined in the presence of 1 µM of neurotensin 1–13. The reaction is halted by filtration and the radioactivity retained on the filter measured by scintillation counting. The products are studied over a range of concentrations in order to determine the 50 % inhibitory concentration for the specific binding. The compounds of formula (I) have, in this test, an $IC_{50}$ of less than 15 µM.

The compounds of formula (II) have a low toxicity compatible with their use as an active principle in medicaments.

The following examples illustrate the invention.

A sample of the A9738 actinomycetes strain was deposited and registered with the Centraalbureau voor Schimmel culturen (CBS) at Baarn (Netherlands) under the conditions of the Treaty of Budapest, 22 Mar. 1994, under the number CBS 162.94.

For the N.M.R. spectra, the nomenclature used is that of the Protein Data Bank, with the exception of the methyl radicals which are known as M. The amino acid residues of the macrocyclic residues of the compounds of formulae (I) and (II) are known as X-TYR1 (N end amino acid), X-ILE2, X-TYR3 and X-TYR4 (C end amino acid). The amino acid residues of the chain are known as R, according to the name of the amino acid and its position in the chain.

EXAMPLE 1

Preparation of the compound of formula (I) in which R, R' and R" represent hydroxyl radicals and R'" represents a hydrogen atom:

A 250 ml medium containing 5 g/l of peptone, 5 g/l of yeast extract, 15 g/l of glucose, 5 g/l of meat extract, 3 g/l of calcium carbonate, 5 g/l of sodium chloride and 1 g/l of agar is seeded, in a 2 liter Erlenmeyer flask, with a slant gelose of A9738 actinomycetes (CBS 162.94) in the form of a spore suspension. After agitating at 140 r/min in a thermostatically controlled agitator at 28° C. for 72 hours, the whole of the culture is transferred under sterile conditions to a primary fermenter filled with 60 liters of the same medium. The fermenter is stirred at 300 r/min, aerated at 5 m$^3$/h and thermostatically controlled at 28° C. for 44 hours. The whole of the culture is then transferred under sterile conditions to a production fermenter with 450 liters of medium sterilized for 40 minutes at 122° C. (distillers 5 g/l, beans 40 g/l, glucose 5 g/l, soybean oil 10 g/l, sodium chloride 5 g/l and cobalt chloride 20 mg/l) and then maintained at a temperature of 28° C. for 94 hours, with stirring at 250 r/min and aerated at the rate of 15 m$^3$/h. The broth (487 liters, pH 7.8) is then stirred with 5 % of clarcel, marketed by CECA, and then filtered in order to separate the mycelium from the filtrate. The filtrate (300 liters) is extracted with 2 times 100 liters of ethyl acetate and the aqueous phase (250 liters) is ultrafiltered through an ultrafiltration membrane whose cut-off threshold is 20 kD, until a retentate volume of 40 liters is obtained. The ultrafiltrate (210 liters) is run through a stainless steel column (20×60 cm) containing 30 liters of Duolite S861 resin marketed by Rhom and Haas with a flow rate of 30 l/h. The column is rinsed with 80 liters of water and chromatography is then carried out by a stepwise methanol/water gradient with a flow rate of 30 l/h and fractions of 10 liters (50/50 by volume for Fractions 1 and 2, 60/40 by volume for Fractions 3 to 8, 80/20 by volume for Fractions 9 and 10 and 100 % methanol for Fractions 11 and 12). Fractions 3 to 6 are combined, the methanol is removed under reduced pressure (3.4 kPa) and the aqueous phase is then lyophilized. 12.4 g of a yellow powder are thus obtained. This lyophilizate is disintegrated in 600 ml of methanol cooled to 40° C., the insoluble material is separated and the solution is concentrated under reduced pressure (3.4 KPa) to give 4 g of dry extract. This extract is dissolved in 110 ml of a methanol/water solution (1/10 by volume) and chromatographed on a stainless steel column (5×60 cm) filled with Matrex C18-grafted silica (20 µ, 60 Å), marketed by Am icon, using a Gilson system. The 50 ml fractions are collected with a Pharmacia fraction collector and the flow rate is 50 ml/minute. The gradient profile used is the following: over 30 minutes, linear gradient from 10/90 by volume methanol/water to 40/60 by volume methanol/water, stationary stage of 30 minutes at 40/60 by volume methanol/water and then a linear gradient from 40/60 by volume methanol/water to 100% methanol over 40 minutes. Fractions 21 to 29 are combined and concentrated under reduced pressure (3.4 kPa) to a volume of 10 ml. This solution is deposited at the top of a glass column (5×30 cm) filled with Macherey Nagel SC6 polyamide. Elution is carried out with water. 50 fractions of variable volumes (20 to 70 ml) are collected. After having set aside Fractions 1 to 12 (approximately 1100 ml), Fractions 13 to 25 (600 ml) are combined and deposited on a glass column with a diameter of 5 cm and containing 250 ml of DEAE Biogel A (Bio-Rad). The elution is carried out with water. The first 900 ml of effluent and eluate are set aside and then the desired product is subsequently eluted with 2 liters of water. These 2 liters are run through an Analytichem International cell with a volume of 75 ml (internal diameter 2.5 cm) containing 40 ml of 40 µ Bondesil C18-grafted silica marketed by Analytichem International. The effluent is set aside and the product is eluted with methanol. The methanolic solution is concentrated under reduced pressure to give 60 mg of pure product of formula (I) in which R, R' and R" represent hydroxyl radicals and R'" represents a hydrogen atom in the form of a slightly yellow powder [IR spectrum: characteristic bands (cm$^{-1}$) at 3395 (phenol OH), 3300 (NH), 2970 (CH3), 2935 (CH2), 2875 (CH3, CH2), 3125 to 2125 (acid OH), 1670 (acid and amide C=O), 1585 to 1500 (benzene rings), 1235 (aromatic ether and phenol CO), 865 and 835 (aromatic CH; Mass spectrum (Finengan TSQ46 in D/Cl with ammonia as reagent gas) M/z=634 MNH$_4^+$, 617 MH$^+$; N.M.R. spectrum (400 MHz, d$_6$-DMSO, δ in ppm): X-TYR1: broad NH2, HA 4.14, HB1, HB2 3.05, 3.20, HD1 7.10, HD2 6.80, HE1 6.81; X-ILE2: NH 8.38, HA 4.20, HB 1.58, MG1 0.88, HG21, HG22 1.20,1.51, MD 0.84; X-TYR3: NH 8.48, HA 3.63, HB1, HB2 2.42, 2.88, HD1 6.60, HD2 5.59; X-TYR4: NH 4.22, HA 4.26, HB1, HB2 3.02, 3.47, HD1 7.24, HD2 7.26, HE1 7.46, HE2 6.78].

EXAMPLE 2

Preparation of the compound of formula (I) in which R represents a methoxy radical, R' and R" represent hydroxyl radicals and R'" represents a hydrogen atom.

200 mg of the compound of formula (I) in which R, R' and R" represent hydroxyl radicals and R'" represents a hydrogen atom are dissolved in 20 ml of methanol and 0.8 ml of concentrated sulphuric acid is added. The solution is stirred for 18 hours at a temperature in the region of 20° C. 10 g of Duolite S 861 (Rhom and Haas) are then added and the mixture is diluted with 200 ml of water and stirred for 30 minutes at a temperature in the region of 20° C. The resin is filtered and washed on sintered glass with 60 ml of water. The compound is then extracted by elution with 100 ml of methanol. After evaporation under reduced pressure (3.4 kPa), the residue is purified by chromatography on 170 ml of carboxymethyl-Triacryl resin (Sepracor), elution being carried out with water and 10 ml fractions being collected. The fractions containing the desired compound are combined and evaporated to dryness to give 40 mg of compound of formula (I) in which R represents a methoxy radical, R'" represents a hydrogen atom and R' and R" represent hydroxyl radicals in the form of a slightly yellow powder [Ionspray mass spectrum on Sciex API III: M/z=631 (MH$^+$); Infrared spectrum (FTIR), in methanol): 3390, 3275, 2960, 2875, 1740, 1660, 1585+1500, 1510, 1215, 865+835 cm$^{-1}$; NMR spectrum (400 MHz, DMSO, Temp.=303K, δ in ppm): X-TYR1: NH2 7.92, HA 4.78, HB1, HB2 3.01, 3.17, HD1 7.09, HD2 6.74, HE1 6.82, X-ILE2: NH 8.63, HA 4.19, HB 1.62, MG1 0.82, HG21, HG22 1.18,1.48, MD 0.79; X-TYR3: NH 8.73, HA 3.58, HB1, HB2 2.42, 2.62, HD1 6.51, HD2 5.50; X-TYR4: NH 4.22, HA 4.45, HB1, HB2 3.21, 3.39, HD1 7.12, HD2 7.36, HE1 7.58, HE2 6.82, OCH$_3$ 3.81].

EXAMPLE 3

Preparation of the compound of formula (I) in which R, R' and R" represent hydroxyl radicals and R'" represents an iodine atom.

740 mg of the compound of formula (I) in which R, R' and R" represent hydroxyl radicals and R'" represents a hydrogen atom are dissolved in 60 ml of methanol and 180 mg of sodium iodide and then 133 mg of 1,2,4,6-tetrachloro-3α, 6α-diphenylglycouril are added. The solution is stirred for 45 minutes at a temperature in the region of 20° C. The solvents are then evaporated under reduced pressure (2 kPa) and the crude reaction mixture is fixed on 10 g of silica gel. This mixture is deposited on a column with a diameter of 4 cm containing 150 g of silica gel and eluted with an ethyl acetate/acetic acid/water mixture (103/12/10 by volume), 100 ml fractions being collected. The fractions between 900 and 2400 ml are combined and concentrated to dryness to give 734 mg of an ochre-coloured solid. This solid is taken up in 20 ml of water and 100 ml of ethyl acetate, warmed to a temperature in the region of 40° C. and then cooled to a temperature in the region of 200° C., before being filtered and washed with 3 ml of water and then with three times 20 ml of ethyl acetate. It is dried under reduced pressure (30 Pa) at 400° C. in order to obtain 387.7 mg of compound of formula (I) in which R, R', R" represent hydroxyl radicals and R'" represents an iodine atom in the form of a beige-coloured solid melting at a temperature above 260° C. [Mass spectrum on an Autospec VG Fisons, in LIMS (Liquid Secondary Ion Mass Spectroscopy), glycerol/thioglycerol matrix: M/z=743 (MH)$^+$; NMR spectrum (600 MHZ, DMSO, Temp. 303 K; chemical shifts in ppm): X-TYR1: HA 3.98, HB1, HB2 3.16, 2.80, HD1, HD2 7.34, 6.67; X-ILE2: NH 8.51, HA 4.18, HB 1.62, MG1 0.84, HG21, HG22 1.49,1.16, MD 0.82; X-TYR3: NH 8.61, HA 3.64, HB1, HB2 2.66, 2.40, HD1, HD2 6.52, 5.29; X-TYR4: NH 4.19, HA 4.27, HB1, HB2 3.39, 3.02, HD1, HD2 7.40, 7.22, HE1, HE2 7.10, 6.70].

EXAMPLE 4

Preparation of the compound of formula (I) in which R, R' and R" represent methoxy radicals and R'" represents a hydrogen atom.

20 ml of a 2M solution of trimethylsilyldiazomethane in hexane are added over one hour, under an inert atmosphere, to a solution of 1.4 g of the compound of the formula (I) in which R, R' and R" represent hydroxyl radicals, R'" represents a hydrogen atom and R$_1$—(R$_2$)$_m$—(R$_3$)$_n$—(R$_4$)$_p$ represents Fmoc- dissolved in 30 ml of methanol and stirring is carried out for 18 hours at a temperature in the region of 200° C. A further 10 ml of a 2M solution of trimethylsilyldiazomethane in hexane are added and stirring is carried out for 24 hours at a temperature in the region of 200° C. 0.5 ml of acetic acid is added and the solvents are evaporated under reduced pressure (2 kPa). The residue obtained is purified by chromatography on a column with a diameter of 4 cm containing 250 g of silica gel, elution being carried out successively with 750 ml of dichloromethane, 3000 ml of a dichloromethane/methanol mixture (98/2 by volume) and then a dichloromethane/methanol mixture (95/5 by volume), 100 ml fractions being collected. The fractions between 2500 and 4400 ml are combined and evaporated to give 932 mg of a white solid. The product can continue to be purified, by dissolving it in 10 ml of dichloromethane and by diluting with 50 ml of ethanol; the solution is then concentrated under reduced pressure at a temperature in the region of 200° C., until precipitation begins, and left standing for 16 hours at a temperature in the region of +5° C. 441 mg of the compound of formula (II) in which R, R' and R" represent methoxy radicals, R'" represents a hydrogen atom and R$_1$—(R$_2$)$_m$—(R$_3$)$_n$—(R$_4$)$_p$ represents Fmoc are thus obtained in the form of a white powder melting at 145° C., with decomposition [Mass spectrum on an Autospec VG Fisons, in LIMS (Liquid Secondary Ion Mass Spectroscopy), glycerol+thioglycerol matrix: M/z=881 (MH)$^+$]. 0.1 ml of piperidine is added to 187 mg of the compound obtained above dissolved in 20 ml of dichloromethane and stirring is carried out at a temperature in the region of 20° C. for 42 hours. The solvents are evaporated under reduced pressure (2 kPa); the residue is triturated in 10 ml of diethyl ether at a temperature in the region of 35° C., cooled to a temperature in the region of 20° C., filtered and washed three times in 5 ml of diethyl ether to give 140 mg of white powder which is taken up in 5 ml of water and extracted five times with 20 ml of ethyl acetate. The solvents are evaporated under reduced pressure (2 kPa). Purification is continued by taking up in 1 ml of dichloromethane diluted with 10 ml of diethyl ether. 80 mg of the compound of formula (I) in which R, R' and R" represent methoxy radicals and R'" represents a hydrogen atom are thus obtained in the form of a slightly yellow powder melting at 2400° C., with decomposition [Mass spectrum on an Autospec VG Fisons, in LIMS (Liquid Secondary Ion Mass Spectroscopy), glycerol+thioglycerol matrix: M/z=659 (MH)$^+$].

EXAMPLES OF THE PREPARATION OF COMPOUNDS OF FORMULA (II):

Example A 61 mg of the derivative of formula (I) in which R, R' and R" represent hydroxyl radicals and R'" represents a hydrogen atom, 64 mg of Fmoc-Arg-Pro-OH and 13 mg of N-hydroxybenzotriazole are dissolved in 1 ml of dimethylformamide containing 4A molecular sieve. After 15 hours, 10 μl of pyridine and 21 mg of dicyclohexylcarbodiimide are added and the mixture is left to react for 72 hours at 40° C. 15 ml of water are then added and the precipitate thus formed is collected on sintered glass No. 4. The solid is disintegrated in 10 ml of methanol and then filtered. The filtrate is diluted to 15 ml and then water (85 ml) is added.

The solution is subjected to high performance liquid chromatography with an octadecyl-grafted silica column (250× 10 mm) at a flow rate of 3.5 ml/minute. The elution is carried out using a linear gradient from water containing 0.07% trifluoroacetic acid to acetonitrile/water (70/30 by volume) containing 0.07% trifluoroacetic acid. 1.7 ml fractions are collected. Those containing the desired product are combined and evaporated under reduced pressure. 0.6 mg of the compound of formula (II) in which R represents a hydroxyl radical, $R_1$—$(R_2)_m$—$(R_3)_n$—$(R_4)_p$ represents Fmoc-Arg-Pro-, $R_5$ and $R_6$ represent hydroxyl radicals and $R_7$ represents a hydrogen atom is thus isolated in the form of a beige powder [Mass spectrum on a Perkin Elmer API III, in ionspray: M/z 1092 $MH^+$ 1114 $MNa^+$; N.M.R. spectrum (400 MHz, DMSO, δ in ppm): R-FMOC1: HA1, HA2 4.22, HB 4.30, aromatic protons 7.70, 7.31, 7.40, 7.89; R-ARG2: NH 7.90, HA 4.20, HB1, HB2 1.45, 1.22, HG1, HG2 1.45, HD1, HD2 2.97, broad guanidine; R-PRO3: HA 4.42, HB1, HB2 1.83,1.88, HG1, HG2 1.88, 1.88, HD1, HD2 3.60, 3.40; X-TYR1: NH 6.98, HA 4.69, HB1, HB2 2.92, HD1 6.90, HD2 6.70, HE1 6.68; X-ILE2: NH 8.27, HA 4.05, HB 1.60, MG1 0.82, HG21, HG22 1.15, 1.55, MD 0.83; X-TYR3: NH 8.65, HA 3.58, HB1, HB2 2.88, 2.40, HD1 6.57, HD2 5.47; X-TYR4: NH 4.27, HA 4.18, HB1, HB2 2.48, 2.52, HD1 7.16, HD2 7.31, HE1 7.51, HE2 6.78].

The peptide Fmoc-Arg-Pro-OH can be synthesized in the solid phase, by using an Fmoc synthesis strategy on an Applied Biosystems 431A device using "standard Fmoc" cycles provided by the manufacturer with N-methyl-2-pyrrolidone as solvent. Deprotection of the α-amine functional groups is carried out with a 20% solution of piperidine in N-methyl-2-pyrrolidone for 20 minutes at each synthesis stage. The peptide is synthesized on 0.25 mmol of 4-hydoxymethylphenoxymethyl/styrene-1% divinylbenzene copolymer (HMP, Applied Biosystems) Wang resin (J. Am. Chem. Soc., 95, 1328 (1973)). The symmetrical anhydride of Fmoc-Pro-OH is formed (1 mmol) by reaction for 20 minutes with 0.5 mmol of dicyclohexylcarbodiimide in 1.3 ml of N-methyl-2-pyrrolidone and 1.8 ml of dichloromethane. After reacting for 13 minutes, 0.36 ml of 0.1M dimethylaminopyridine in dimethylformamide are added. After removal by filtration of the dicyclohexylurea formed, the symmetrical anhydride is reacted for 30 minutes with the resin. The amine functional group of the proline is deprotected by reaction for 20 minutes with a 20% solution of piperidine with N-methyl-2-pyrrolidone. The N-hydroxybenzotriazolyl ester of Fmoc-Arg(Pmc)-OH is formed by reaction of 1 mmol of Fmoc-Arg(Pmc)-OH in 4.1 ml of N-methyl-2-pyrrolidone in the presence of 1 mmol of N-hydroxybenzotriazol and 1 mmol of dicyclohexylcarbodiimide for 20 minutes. After removal of the dicyclohexylurea formed, the ester is reacted for 30 minutes with the resin. A resin is thus obtained on which is grafted the Fmoc-Arg(Pmc)-Pro group. The peptide is cleaved from the resin by treatment for 1 hour and 30 minutes with 10 ml of trifluoroacetic acid, 0.75 g of phenol, 0.25 ml of ethanedithiol, 0.5 ml of thioanisole and 0.5 ml of water per 100 mg of peptidylresin. After removal of the resin by filtration, the liquid phase is concentrated on a rotary evaporator for 30 minutes under reduced pressure (4 kPa). The peptide is then precipitated by addition of tert-butyl methyl ether and petroleum ether (4/1 by volume) and recovered by centrifuging. The peptide is taken up in a minimum volume of trifluoroacetic acid, precipitated by addition of a mixture of tert-butyl methyl ether and petroleum ether (4/1 by volume) and recovered by centrifuging, this operation is repeated twice. The peptide is then washed with 30 ml of a mixture of tert-butyl methyl ether and petroleum ether (4/1 by volume), recovered by centrifuging and dried under vacuum (4 kPa). The peptide is used as is in the following stages of the synthesis.

Example B

A solution of 60 mg of Fmoc-Arg-Arg-Pro-OH, 16 mg of N-hydroxysuccinimide and 20 mg of dicyclohexylcarbodiimide in 1.5 ml of dimethylformamide is heated for 15 hours at 50° C. 50 mg of the derivative of formula (I) in which R, R' and R" represent hydroxyl radicals and R'" represents a hydrogen atom and one drop of pyridine are then added and the mixture is left to react for 72 hours at a temperature of 50° C. The reaction mixture is deposited at the top of a silica column (2.6×6 cm) equilibrated in dichloromethane. After washing the dichloromethane (45 ml), the column is run through with an ethyl acetate/acetic acid/water mixture (60/12/10 by volume). 4.5 ml fractions are collected. The fractions containing the desired product are combined and evaporated to dryness under reduced pressure (3.4 kPa) to give 10 mg of a beige powder. This powder is subjected to high performance liquid chromatography with an octadecyl-grafted silica column (250×10 mm) at a flow rate of 3.5 ml/minute. Elution is carried out using a linear gradient from water containing 0.07% of trifluoroacetic acid to acetonitrile/water (70/30 by volume) containing 0.07% of trifluoroacetic acid. 1.7 ml fractions are collected. Those containing the desired product are combined and evaporated under reduced pressure to give 5 mg of the compound of formula (II) in which R represents a hydroxyl radical, $R_1$—$(R_2)_m$—$(R_3)_n$—$(R_4)_p$ represents Fmoc-Arg-Arg-Pro-, $R_5$ and R6 represent hydroxyl radicals and $R_7$ represents a hydrogen atom in the form of a slightly beige powder [Mass spectrum on a Perkin Elmer API III, in ionspray: M/z: 1248 $MH^+$, 624.8 $(M+2H)^{++}$; N.M.R. Spectrum (400 MHz, DMSO, δ in ppm: R-Fmoc1: HA1, HA2 4.28, 4.32, HB 4.32, aromatic protons 7.68, 7.32, 7.42, 7.88; R-ARG2: NH 7.30, HA 4.08, HB1, HB2 1.65, 1.50, HG1, HG2 1.50, HD1, HD2 3.15, guanidine 7.35, 6.90; R-ARG3: NH 7.98, HA 4.48, HB1, HB2 1.50, HG1, HG2 1.50, HD1, HD2 3.10, guanidine 7.22, 6.90; R-PRO4: HA 4.38, HB1, HB2 1.85, 1.95, HG1, HG2 1.85,1.95, HD1, HD2 3.45, 3.61; X-TYR1: NH 6.90, HA 4.92, HB1, HB2 2.98, HD1 6.90, HD2 6.90, HE1 6.80; X-ILE2: NH 8.12, HA 4.13, HB 1.63, MG1 0.85, HG21, HG22 1.22, 1.51, MD 0.83; X-TYR3: NH 8.48, HA 3.62, HB1, HB2 2.65, 2.70, HD1 6.58, HD2 5.52; X-TYR4- NH 4.22, HA 4.32, HB1, HB2 3.20, 3.35, HD1 7.28, HD2 7.30, HE1 7.51, HE2 6.78].

The synthesis of the peptide Fmoc-Arg-Arg-Pro-OH is carried out as described for the peptide Fmoc-Arg-Pro-OH in Example A. A resin on which a group Fmoc-Arg(Pmc)-Pro has been grafted beforehand as described in Example A is deprotected from its Fmoc protective group with 20% piperidine in N-methyl-2-pyrrolidone for only 3 minutes in order to restrict formation of a corresponding diketopiperazine derivative. The resin is washed copiously with N-methyl-2-pyrrolidone. In parallel, the N-hydroxybenzotriazolyl ester of Fmoc-Arg(Pmc)-OH is formed by reaction of 1 mmol of Fmoc-Arg(Pmc)-OH in 2.1 ml of N-methyl-2-pyrrolidone, 1 ml of 1M N-hydroxybenzotriazole in N-methyl-2-pyrrolidone and 1 ml of 1M dicyclohexylcarbodiimide in N-methyl-2-pyrrolidone for 20 minutes. After removal of the dicyclohexylurea formed, this ester is reacted for 30 minutes with the grafted resin. A resin on which the group Fmoc-Arg (Pmc)-Arg(Pmc)-Pro is grafted is thus obtained. The peptide Fmoc-Arg-Arg-Pro-OH is cleaved from the resin and purified in the same way as Fmoc-Arg-Pro-OH.

Example C 7 mg of the product of Example B are dissolved in 180 µl of dimethylformamide and 20 µl of piperidine are added. The solution quickly becomes cloudy and a precipitate appears. The precipitate is collected by centrifuging and washed with two times 200 µl of acetonitrile. 1 mg of the compound of formula (II) in which R represents a hydroxyl radical, $R_1$—$(R_2)_m$—$(R_3)_n$—$(R_4)_p$ represents H-Arg-Arg-Pro-, $R_5$ and $R_6$ represent hydroxyl radicals and $R_7$ represents a hydrogen atom, in the form of the piperidine salt, is thus obtained [Mass spectrum on a Perkin Elmer API III, in ionspray: M/z 1026 MH$^+$].

Example D 50.3 mg of pentafluorophenyl N-Fmoc-L-prolinate are added to a solution of 62 mg of compound of formula (I) in which R, R' and R" represent hydroxyl radicals and R'" represents a hydrogen atom and 52.5 µl of diisopropylethylamine in 3 ml of dimethylformamide and stirring is carried out for 18 hours at a temperature in the region of 25° C. Dilution is then carried out with 25 ml of ethyl acetate and 25 ml of water and acidification is then carried out with a 1 N aqueous hydrochloric acid solution. After separation by settling, the organic phase is washed with three times 25 ml of water and dried over magnesium sulphate. After filtration, washing and evaporation of the filtrate (2 kPa), 80 mg of solid are obtained. This solid is purified by high performance liquid chromatography on a LiChroprep diol column (Merck) with a diameter of 2.5 cm and a length of 31 cm, the elution being carried out at a flow rate of 10 ml per minute, first with 200 ml of a dichloromethane/ethanol mixture (95/5 by volume) and then 200 ml of a dichloromethane/ethanol mixture (93/7 by volume). The fractions containing the expected compound are combined and evaporated to dryness (2 kPa) to give 25 mg of the compound of formula (II) in which R represents a hydroxyl radical, $R_1$—$(R_2)_m$—$(R_3)_n$—$(R_4)_p$ represents Fmoc-Pro-, $R_5$ and $R_6$ represent hydroxyl radicals and $R_7$ represents a hydrogen atom in the form of a white solid [Mass spectrum (Autospec VG Fisons, in LSIMS): M/z=936 (M+H)$^+$, M/z=714 (M−Fmoc+2H)$^+$; Infrared spectrum (KBr): 3390, 2965, 2930, 2875, 3100 to 2250, 1680, 1585, 1450, 1505, 835, 760 and 740 cm$^{-1}$; NMR spectrum (600 MHz, DMSO, Temp.=350 K, δ in ppm: R-Fmoc1: HA1, HA2 4.20, 4.32, HB 4.32, aromatic protons 7.83, 7.28,7.48,7.88; R-PRO2: HA 4.22, HB1, HB2 1.74, 2.08, HG1, HG2 1.78, 1.95, HD1, HD2 3.28, 3.35; X-TYR1: NH 7.62, HA 4.71, HB1, HB2 2.91, 3.06, HD1 6.89, HD2 6.84, HE1 6.68; X-ILE2- NH 7.95, HA 4.15, HB 1.62, MG1 0.82, HG21, HG22 1.12,1.47, MD 0.79; X-TYR3: NH 8.24, HA 3.62, HB1, HB2 2.46, 2.70, HD1 6.62, HD2 5.52; X-TYR4: NH 4.22, HA 4.26, HB1, HB2 3.10, 3.38, HD1 7.18, HD2 7.25, HE1 7.45, HE2 6.78].

Example E 9 mg of the compound of Example D are dissolved in 0.5 ml of a dichloromethane/piperidine mixture (90/10 by volume). After 96 hours at a temperature in the region of 25° C., the solvents are evaporated under reduced pressure (2 kPa). The residue is taken up in 0.5 ml of water and then washed with two times 1 ml of diethyl ether. The aqueous phase is brought to a pH in the region of 4 with acetic acid. The suspension obtained is then chromatographed on a preparative high performance liquid chromatography column containing Bio-Rad 100 Å octadecyl-grafted silica at a length of 25 cm and a diameter of 1 cm with a flow rate of 6 ml per minute. Elution is carried out using a linear gradient from water/trifluoroacetic acid (100/0.07 by volume) to water/acetonitrile/trifluoroacetic acid (63/37/0.07 by volume), over 33 minutes. 3 ml fractions are collected. The fractions containing the desired product are combined, frozen to −80° C. and lyophilized (1 Pa) to give 0.6 mg of compound of formula (II) in which $R_1$—$(R_2)_m$—$(R_3)_n$—$(R_4)_p$ represents H-Pro-, R, $R_5$ and $R_6$ represent hydroxyl radicals and $R_7$ represents a hydrogen atom in the form of a white solid [Mass spectrum (Finnegan TSQ46, in chemical ionization desorption with ammonia as reagent gas): M/z= 714 (MH$^+$); NMR spectrum (600 MHz, DMSO, Temp.=303 K, δ in ppm): R-PRO1: HA 4.10, HB1, HB2 1.77,2.12, HG1, HG2 1.73, HD1, HD2 3.20; X-TYR1: NH 8.13, HA 4.78, HB1, HB2 2.94, 3.03, HD1 6.78, HD2 6.78, HE1 6.71; X-ILE2: NH 8.31, HA 4.10, HB 1.62, MG1 0.82, HG21, HG22 1.12,1.47, MD 0.79; X-TYR3: NH 8.66, HA 3.59, HB1, HB2 2.42, 2.69, HD1 6.58, HD2 5.49; X-TYR4: NH 4.14, HA 4.31, HB1, HB2 3.10, 3.38, HD1 7.18, HD2 7.32, HE1 7.52, HE2 6.80].

Example F 20 mg of compound of formula (I) in which R represents a methoxy radical, R' and R" represent hydroxyl radicals and R'" represents a hydrogen atom are added to a mixture of 23.2 mg of (Boc)$_2$Lys-Ψ[CH$_2$NH]-Lys(Boc)-Pro-OH trifluoroacetate, 11.4 mg of 2-[1H-benzotriazol-1-yl]-1,1,3, 3-tetramethyluronium hexafluoromethylphosphate and 16 µl of diisopropylethylamine in 3 ml of dimethylformamide at a temperature in the region of 20° C. The mixture is stirred for 6 hours and 30 minutes at this same temperature. The solvents are evaporated under reduced pressure (15 Pa). The residue is taken up in 5 ml of dichloroethane and washed with two times 1 ml of water, two times 1 ml of a 0.1M sodium monophosphate solution, two times 1 ml of a 0.25M sodium hydrogencarbonate solution and with two times 1 ml of water. The organic phase is concentrated under reduced pressure (5.3 kPa). The residue is taken up in 2 ml of aqueous trifluoroacetic acid (95/5 by volume) at a temperature in the region of 20° C. for 1 hour and 30 minutes. After concentrating to a volume of approximately 0.2 ml (5.3 kPa), the product is precipitated by addition of methyl tert-butyl ether and collected by centrifuging. 2.2 mg of compound of formula (II) in which $R_1$—$(R_2)_m$—$(R_3)_n$—$(R_4)_p$ represents H-Lys-Ψ[CH$_2$NH]-Lys-Pro-, R represents a methoxy radical, $R_5$ and R6 represent hydroxyl radicals and $R_7$ represents a hydrogen atom are thus obtained with a pale yellow colour. [Mass spectrum on Sciex API III, in ionspray: M/z=970 (MH$^+$)]

The compound (Boc)$_2$Lys-Ψ[CH$_2$NH]-Lys(Boc)-Pro-OH can be prepared according to the method of S. Doulut et al., Peptide Research, 5(1), 30–38 (1992), by reacting (Boc)$_2$ Lysinal with H-Lys(Boc)-Pro-OBg and then by saponifying the end ester (OBg ester=N-benzhydrylglycolamide ester: Tetrahedron, 44, 5101–5108 (1988)).

Example G 37 mg of compound as described in Example F are dissolved in 0.6 ml of dioxane, 0.3 ml of water and 0.3 ml of 1M lithium hydroxide solution at a temperature in the region of 0° C. After stirring for 70 minutes at a temperature in the region of 0° C., dilution is carried out with 10 ml of aqueous acetic acid (90/10 by volume) and the crude product is injected onto a preparative high performance liquid chromatography column containing Bio-Rad RSL 100 Å octadecyl-grafted silica with a length of 30 cm and a diameter of 1 cm. Elution is carried out using a linear gradient from water/trifluoroacetic acid (100/0.07 by volume) to water/acetonitrile/trifluoroacetic acid (65/35/0.07 by volume), over 30 minutes. The fractions containing the desired product are combined, frozen to −80° C. and lyophilized (1 Pa) to give 4.4 mg of the compound of formula (II) in which $R_1$—$(R_2)_m$—$(R_3)_n$—$(R_4)_p$ represents H-Lys-Ψ[CH2NH]-Lys-Pro-, R, $R_5$ and $R_6$ represent hydroxyl radicals and R7 represents a hydrogen atom in the form of a white powder [Mass spectrum on Sciex API III, in ionspray: M/z=956 (MH$^+$)].

Example H

The solid-phase synthesis is carried out using the equipment from the company Shandon (Life Science International Group), with the exception of the rotator for haemolysis tubes. The resin is confined in 3 ml high-density polyethylene (HDPE) syringes for solid-phase extraction equipped with teflon filters. These syringes are fitted to a two-way teflon valve and are closed by a disposable HDPE finned stopper. Agitation of the syringes is carried out on a rotator for haemolysis tubes. The washing and filtration operations are carried out on a work station for solid-phase extraction (vacuum chamber equipped with Luer fittings, Shandon).

The synthesis is carried out on 50 μmol of resin in Fmoc chemistry. The couplings of the amino acids are carried out by treating the resin for 1 hour with 250 μmol of the suitably protected amino acid in the presence of 250 μmol of 2-(1H-benzotriazole-1-yl)-1,1,3,3-tetramethyluronium hexafluorophosphate, 250 μmol of N-hydroxybenzotriazole and 750 μmol of diisopropylethylamine in 1.2 ml of an N-methyl-2-pyrrolidone-dimethylformamide mixture (1/1 by volume). Deprotection of the Fmoc group is carried out by 3 successive treatments of the resin, for 1 minute, 1 minute and 20 minutes respectively, with 2 ml of a 20% by volume solution of piperidine in N-methyl-2-pyrrolidone.

50 μmol of Fmoc-Gly-resin [Wang resin] (Wang et al., J. Amer. Chem. Soc., 95, 1328 (1973)) are subjected successively to the following treatments:

Deprotection of the Fmoc group,

Washing in 5 times 2 ml of N-methyl-2-pyrrolidone,

Coupling of 2 equivalents of the compound of formula (I) in which R, R' and R" each represent a hydroxyl radical and R'" represents a hydrogen atom, the amino of which is protected by Fmoc, Washing with 5 times 2 ml of N-methyl-2-pyrrolidone, Deprotection of the Fmoc group, Washing with 5 times 2 ml of N-methyl-2-pyrrolidone, Coupling of 5 equivalents of Fmoc-proline, Washing with 5 times 2 ml of N-methyl-2-pyrrolidone, Deprotection of the Fmoc group, Washing with 5 times 2 ml of N-methyl-2-pyrrolidone, Coupling of 5 equivalents of Fmoc-arginine(Pmc), Washing with 5 times 2 ml of N-methyl-2-pyrrolidone, Deprotection of the Fmoc group, Washing with 5 times 2 ml of N-methyl-2-pyrrolidone, Coupling of 5 equivalents of Fmoc-arginine(Pmc), Washing with 5 times 2 ml of N-methyl-2-pyrrolidone, and the peptide is then cleaved by reaction in 10 ml of a trifluoroacetic acid/phenol/ethanedithiol/thioanisole/water mixture (4013111212 by volume) for 90 minutes. The resin is removed by filtration. The filtrate is concentrated under reduced pressure using a rotary evaporator equipped with a membrane pump and a dry ice trap for 1 hour, the temperature of the bath being maintained at 45° C. The final volume of the concentrate is approximately 1 ml. The product is precipitated by addition of 15 ml of methyl tert-butyl ether and collected by centrifuging. The pellet is dissolved in 1 ml of trifluoroacetic acid, precipitated by addition of 15 ml of methyl tert-butyl ether and then washed with 15 ml of a methyl tert-butyl ether/petroleum ether mixture (2/1 by volume) in the presence of 0.2 ml of trifluoroacetic acid. The product is dried under reduced pressure (3.5 kPa), then purified by high performance liquid chromatography on a 100 Å $C_{18}$ column (250×10 mm, Bio-Rad), elution being carried out with a gradient from 20 to 40% of acetonitrile containing 0.07% by volume of trifluoroacetic acid in water containing 0.07% by volume of trifluoroacetic acid at a flow rate of 6 ml/minute, over 30 minutes, and then lyophilized. 3.4 mg of the ditrifluoroacetate of the compound of formula (II) in which R represents an —NH—$CH_2$—COOH radical, $R_1$—$(R_2)_m$—$(R_3)_n$—$(R_4)_p$ represents Fmoc-Arg-Arg-Pro-, $R_5$ and $R_6$ represent hydroxyl radicals and $R_7$ represents a hydrogen atom are thus obtained in the form of a white powder [Mass spectrum on Sciex API III, in ESMS (Electrospray Mass Spectrometry): M/z=1306 (MH)$^+$, M/z=653 (M+2H)$^{2+}$].

Example I 180 mg (170 μmol) of Boc-Arg(benzyloxycarbonyl)$_2$-Arg (benzyloxycarbonyl)-$_2$-Pro-OH are treated with 31 mg (150 μmol) of dicyclohexylcarbodiimide and 23 mg (170 μmol) of N-hydroxybenzotriazole in 3 ml of dimethylformamide for 4 hours at a temperature in the region of 200° C. The dicyclohexylurea formed is then filtered on a 0.45 μm Millex HV filter (Millipore) and the filtrate is added to a solution containing 100 mg (162 μmol) of the compound of formula (I) in which R'" represent hydrogen atoms and R, R' and R" represent hydroxyl radicals and 0.025 ml (143 μmol) of diisopropylethylamine in 2.5 ml of dimethylformamide. The reaction is carried out for 24 hours at a temperature in the region of 20° C. The solvent is removed by virtue of a Speed Vac (Savant) centrifugal evaporator equipped with a vane pump for 18 hours at a temperature in the region of 20° C. The residue is dissolved in 20 ml of dichloromethane and the solution extracted successively with 2 times 4 ml of distilled water, 2 times 4 ml of a 0.1M solution of sodium dihydrogenphosphate in distilled water and 2 times 4 ml of distilled water. The compound of formula (II) in which $R_1$—$(R_2)_m$—$(R_3)_n$—$(R_4)_p$ represents Boc-Arg(benzyloxycarbonyl)$_2$-Arg (benzyloxycarbonyl)$_2$-Pro-, R, $R_5$ and $R_6$ represent hydroxyl radicals and $R_7$ represents a hydrogen atom is thus obtained in solution in dichloromethane. This solution is divided into three equal parts which are dried. One of these parts is dissolved in 2 ml of a dichloromethane/methanol mixture (1/1 by volume). 100 mg of 10% palladium-on-charcoal and 100 mg of ammonium formate are added to this solution. The reaction is carried out for 100 minutes with periodic stirring to a vortex. The reaction medium is then filtered on a 0.45 μm Millex HV filter (Millipore) and the filter washed with 5 ml of methanol. The solvent is evaporated under reduced pressure (2.6 kPa, 450° C., 30 minutes). The product is finally purified by high performance liquid chromatography on a 100 Å $C_{18}$ column (250×10 mm, Bio-Rad), elution being carried out with a gradient from 15 to 40% of acetonitrile containing 0.07% of trifluoroacetic acid (by volume) in water containing 0.07% of trifluoroacetic acid (by volume) at a flow rate of 6 ml/minute over 30 minutes, and then lyophilized. 15.2 mg of the compound of formula (I) in which $R_1$—$(R_2)_m$—$(R_3)_n$—$(R_4)_p$ represents Boc-Arg-Arg-Pro-, R, $R_5$ and $R_6$ represent hydroxyl radicals and $R_7$ represents a hydrogen atom are thus obtained in the form of a white powder [Mass spectrum on Sciex API III, in ESMS (Electrospray Mass Spectrometry): M/z=1126 (MH)⁺, M/z= 563 (M+2H)²⁺].

The peptide Boc-Arg(benzyloxycarbonyl)$_2$-Arg (benzyloxycarbonyl)$_2$-Pro-OH can be prepared in the following way: the compound Boc-Arg(benzyloxycarbonyl)$_2$-OH is reacted with methyl prolinate in the presence of 2-(1H-benzotriazole-1-yl)-1,1,3,3-tetramethyluronium hexafluorophosphate in acetonitrile or dimethylformamide, diisopropylethylamine being used as base in order to obtain a pH above 8, and the Boc group is then cleaved with 40% trifluoroacetic acid in dichloromethane. The compound Boc-Arg(benzyloxycarbonyl)$_2$-OH is reacted with this product in the presence of 2-(1H-benzotriazole-1-yl)-1,1,3,3-tetramethyluronium hexafluorophosphate in acetonitrile or dimethylformamide, diisopropylethylamine being used as base in order to obtain a pH above 8. The ester obtained can then be saponified with lithium hydroxide at a temperature in the region of +40° C.

Example J

One of the 3 parts of the compound of formula (II) in which $R_1$-$(R_2)_m$—$(R_3)_n$—$(R_4)_p$ represents Boc-Arg (benzyloxycarbonyl)$_2$-Arg(benzyloxycarbonyl)$_2$-Pro-, R, $R_5$ and $R_6$ represent hydroxyl radicals and $R_7$ represents a hydrogen atom obtained in Example I is treated for 90 minutes with 5 ml of a trifluoroacetic acid/distilled water mixture (95/5 by volume). The medium is then brought to dryness on a rotary evaporator (2.6 kPa, 450° C., 45 minutes) and 15 ml of distilled water are then added to the medium. The suspension obtained is frozen to −80° C. and then lyophilized (96 hours). The product is dissolved in 1 ml of dimethylformamide containing 0.0625 ml of diisopropylethylamine (0.36 mmol). 50 1l (50 ,mol) of a solution of 1-adamantylacetic acid chloride (obtained by reaction of 38.8 mg (200 μmol) of 1-adamantylacetic acid with 17.2 ml (200 μmol) of oxalyl chloride in 200 μl of dichloromethane in the presence of a drop of dimethylformamide for 15 minutes at a temperature in the region of 20° C.) are then added to the peptide solution and the reaction is carried out at a temperature in the region of 20° C. for 1 hour. The solvent is then removed by virtue of a Speed Vac (Savant) centrifugal evaporator equipped with a vane pump for 18 hours at a temperature in the region of 20° C. The residue is dissolved in 2 ml of a dichloromethane/methanol mixture (1/1 by volume) and then 100 mg of 10% palladium-on-charcoal and 100 mg of ammonium formate are added. The reaction is carried out for 150 minutes with periodic stirring to a vortex. The reaction medium is filtered on a 0.45 μm Millex HV filter (Millipore) and the filter washed with 5 ml of methanol. The solvent is then evaporated under reduced pressure (2.6 kPa, 450° C., 30 minutes). The product is finally purified by high performance liquid chromatography on a 100 Å $C_{18}$ column (250×10 mm, Bio-Rad), elution being carried out with a gradient from 15 to 40% of acetonitrile containing 0.07% of trifluoroacetic acid (by volume) in water containing 0.07% of trifluoroacetic acid (by volume) at a flow rate of 6 ml/minute, over 30 minutes, and then lyophilized. 2.9 mg of the ditrifluoroacetate of the compound of formula (II) in which $R_1$—$(R_2)_m$—$(R_3)_n$—$(R_4)_p$ represents 1-adamantylacetyl-Arg-Arg-Pro-, R, $R_5$ and $R_6$ represent hydroxyl radicals and $R_7$ represents a hydrogen atom are thus obtained in the form of a white powder [Mass spectrum on Sciex API III, in ESMS (Electrospray Mass Spectrometry): M/z=601.6 (M+2H)²⁺].

Example K

One of the 3 parts of the compound of formula (II) in which in which $R_1$—$(R_2)_m$—$(R_3)_n$—$(R_4)_p$ represents Boc-Arg(benzyloxycarbonyl)$_2$-Arg(benzyloxycarbonyl)$_2$-Pro-, R, $R_5$ and $R_6$ represent hydroxyl radicals and $R_7$ represents a hydrogen atom obtained in Example I is treated for 90 minutes with 5 ml of a trifluoroacetic acid/distilled water mixture (95/5 by volume). The medium is then brought to dryness on a rotary evaporator (2.6 kPa, 450° C., 45 minutes). 15 ml of distilled water are added to the residue and the suspension is frozen to −80° C. and then lyophilized (96 hours). The product obtained is dissolved in 1 ml of dimethylformamide containing 62.5 μl of diisopropylethylamine (0.36 mmol). 9.9 mg (50 μmol) of 1-adamantylcarboxylic acid chloride are then added to the peptide solution and the reaction is carried out at a temperature in the region of 200° C. for 1 hour. The solvent is then removed by virtue of a Speed Vac (Savant) centrifugal evaporator equipped with a vane pump for 18 hours at a temperature in the region of 20° C. The residue is dissolved in 2 ml of a dichloromethane/methanol mixture (1/1 by volume) and then 100 mg of 10% palladium-on-charcoal and 100 mg of ammonium formate are added. The reaction is carried out for 150 minutes with periodic stirring to a vortex. The reaction medium is then filtered on a 0.45 μm Millex HV filter (Millipore) and the filter washed with 5 ml of methanol. The solvent is evaporated under reduced pressure. The product is finally purified by high performance liquid chromatography on a 100 Å $C_{18}$ column (250×10 mm, Bio-Rad), elution being carried out with a gradient from 18 to 43% of acetonitrile containing 0.07% of trifluoroacetic acid (by volume) in water containing 0.07% of trifluoroacetic acid (by volume) at a flow rate of 6 ml/minute, over 30 minutes, and then lyophilized. 3.1 mg of the ditrifluoroacetate of the compound of formula (II) in which $R_1$—$(R_2)_m$—$(R_3)_n$—$(R_4)_p$ represents 1-adamantylcarbonyl-Arg-Arg-Pro-, R, $R_5$ and $R_6$ represent hydroxyl radicals and $R_7$ represents a hydrogen atom are thus obtained in the form of a white powder [Mass spectrum on a Sciex API III, in ESMS (Electrospray Mass Spectrometry): M/z=594.5 (M+2H)²⁺].

Example L 100 mg (85 μmol) of Fmoc-Arg(Pmc)-Arg(Pmc)-Pro-OH are treated with 17.4 mg of dicyclohexylcarbodiimide (85 μmol) and 12.2 mg of N-hydroxybenzotriazole (90 μmol) in 1.5 ml of dimethylformamide for 4 hours at a temperature in the region of 20° C. The dicyclohexylurea formed is then filtered on a 0.45 μm Millex HV filter (Millipore) and the filter is washed with 0.5 ml of dimethylformamide. 0.45 ml of the filtrate obtained (corresponding to 19 μmol of Fmoc-Arg(Pmc)-Arg(Pmc)-Pro-OH) is then added to 0.25 ml of a solution containing 16.7 mg (22.5 μmol) of the compound of formula (II) in which R, $R_5$ and R6 represent hydroxyl radicals and $R_7$ represents an iodine atom and 4 μl (23 μmol) of diisopropylethylamine in dimethylformamide. The reaction is carried out for 3 hours at a temperature in the region of 200° C. The solvent is removed by virtue of a Speed Vac (Savant) centrifugal evaporator equipped with a vane pump for 18 hours at a temperature in the region of 200° C. The residue is then taken up in 5 ml of a trifluoroacetic acid/phenol/ethanedithiol/thioanisole/water mixture (40/311/2/2 by volume) and left to react for 90 minutes at a temperature in the region of 20° C., with stirring. The mixture is then concentrated on an RC10–10 (Jouan) centrifugal evaporator equipped with a vane pump for 45 minutes (temperature of the evaporating chamber 50° C., trapping of the vapours at −90° C). 15 ml of a tert-butyl methyl ether/petroleum ether mixture (1/1 by volume) are added to the concentrate obtained (approximately 1 ml) in order to precipitate the peptide. The precipitate is collected by centrifuging and dissolved in 1 ml of trifluoroacetic acid. The precipitation operation is repeated once. The peptide is dried under reduced pressure (3.5 kPa). The product is finally purified by high performance liquid chromatography on a 100 Å $C_{18}$ column (250×10 mm, Bio-Rad), elution being carried out with a gradient from 22 to 47% of acetonitrile containing 0.07% of trifluoroacetic acid (by volume) in water containing 0.07% trifluoroacetic acid (by volume) at a flow rate of 6 ml/minute, over 30 minutes, and then lyophilized. 10 mg of the ditrifluoroacetate of the compound of formula (II) in which $R_1$—$(R_2)_m$—$(R_3)_n$—$(R_4)_p$ represents Fmoc-Arg-Arg-Pro-, R, $R_5$ and $R_6$ represent hydroxyl radicals and $R_7$ represents an iodine atom are thus obtained in the form of a white powder [Mass spectrum on Sciex API III, in ESMS (Electrospray Mass Spectrometry): M/z=1374, (M+H)$^+$, M/z=687 (M+2H)$^{2+}$].

The compound Fmoc-Arg(Pmc)-Arg(Pmc)-Pro-OH can be prepared in the following way: Fmoc-Pro-chlorotrityl resin is obtained by treating 0.3 mmol of chlorotrityl chloride/polystyrene-1% divinylbenzene copolymer resin (Novabiochem) with 1 mmol of Fmoc-proline in 3.5 ml of a dichloromethane/diisopropylethylamine mixture (6/1 by volume) for 30 minutes at a temperature in the region of 20° C. 2 ml of methanol are then added and the reaction is left to continue for 30 minutes at a temperature in the region of 20° C. The resin is then washed successively with 3 times 5 ml of methanol and 3 times 5 ml of dichloromethane and dried.

The peptide Fmoc-Arg(Pmc)-Arg(Pmc)-Pro-OH is assembled on an Applied Biosystems 431A device by using the "standard Fmoc" cycles provided by the manufacturer, N-methyl-2-pyrrolidone being used as solvent. Deprotection of the α-amine functional groups is carried out by 20% piperidine in N-methyl-2-pyrrolidone for 20 minutes at each stage in the synthesis. The Fmoc-Pro-chlorotrityl resin is deposited in the reactor of the device. After deprotection of the α-amine functional group of the proline, the N-hydroxybenzotriazolyl ester of Fmoc-Arg(Pmc) is formed by reaction of 1 mmol of Fmoc-Arg(Pmc)-OH in 2.1 ml of N-methyl-2-pyrrolidone, 1 ml of 1M N-hydroxybenzotriazole in N-methyl-2-pyrrolidone and 1 ml of 1M dicyclohexylcarbodiimide in N-methyl-2-pyrrolidone for 20 minutes. After removal of the dicyclohexylurea formed, the ester is reacted for 30 minutes with the resin. The a-amino functional group of the arginine is then deprotected and the N-hydroxybenzotriazolyl ester of Fmoc-Arg(Pmc)-OH is coupled to the resin as described above. The peptide Fmoc-Arg(Pmc)-Arg(Pmc)-Pro-OH is detached from the resin by treating the latter for 15 minutes with 10 ml of an acetic acid/trifluoroethanol/dichloromethane mixture (1/2/7 by volume) at a temperature in the region of 20° C. The resin is then washed successively with 10 ml of dichloromethane and 10 ml of acetonitrile. The organic phases are combined and the solvents are removed on a rotary evaporator (2.6 kPA, 1 hour, 45° C). The residue is taken up in 1 ml of acetonitrile and 30 ml of distilled water are added. The suspension obtained is frozen to −80° C. and lyophilized. 102 mg of Fmoc-Arg(Pmc)-Arg(Pmc)-Pro-OH are thus obtained

Example M 3.06 g of the compound of formula (I) in which R, R' and R" represent hydroxyl radicals and R'" represents a hydrogen atom are dissolved in 80 ml of a 5% aqueous sodium carbonate solution, to which 1.8 g of 9-fluorenylmethyl N-succinyl carbonate and then 40 ml of dioxane are added. The reaction is continued for 5 hours at a temperature in the region of 200° C. The reaction mixture is extracted with 2 times 100 ml of ethyl acetate; the organic phases are removed and the aqueous phase is then acidified to a pH between 1 and 2 with a concentrated hydrochloric acid solution. Extraction is carried out with 3 times 100 ml of ethyl acetate and the organic phases are combined, dried with sodium sulphate, filtered over silica gel and then evaporated under reduced pressure (2 kPa). The precipitate is disintegrated in 300 ml of a methyl tert-butyl ether/methylene chloride mixture (1/1 by volume) and then dried under reduced pressure to give 3.3 g of the compound of formula (II) in which $R_1$—$(R_2)_m$—$(R_3)_n$—$(R_4)_p$ represents Fmoc, R, $R_5$ and $R_6$ represent hydroxyl radicals and $R_7$ represents a hydrogen atom in the form of a white powder [Mass spectrum on Sciex API III, in ESMS (Electrospray Mass Spectrometry): M/z=861 (M+Na)$^+$, M/z=839 (M+H)$^+$; Infrared spectrum (FMIR in methanol): 3395, 3335, 2970, 2940, 2880, 3125 to 2125, 1700, 1665, 1590, 1500, 1450 and 1225; NMR spectrum (400 MHz, DMSO, Temp.=297K, δ in ppm): R-Fmoc-1: HA1, HA2 4.23, HB 4.48, HG1, HG2 7.70, HD1, HD2 7.37, HE1, HE2 7.45, HZ1, HZ2 7.92; X-TYR1: NH 5.73, HA 4.52, HB1, HB2 2.93, 3.03, HD1 6.70, HD2 6.72 HE1 6.70; X-ILE2: NH 8.36, HA 4.12, HB 1.62, MG1 0.83, HG21, HG22 1.18,1.49, MD 0.83; X-TYR3: NH 8.67, HA 3.58, HB1, HB2 2.45, 2.79, HD1 6.57, HD2 5.51; X-TYR4: NH 4.17, HA 4.28, HB1, HB2 3.18, 3.43, HD1 7.19, HD2 7.31, HE1 7.52, HE2 6.80].

Example N 100 mg of Fmoc-Arg(Pmc)-Arg(Pmc)-Pro-OH (85 µmol) are treated with 17.4 mg of dicyclohexylcarbodiimide (85 µmol) and 12.2 mg of N-hydroxybenzotriazole (90 µmol) in 1.5 ml of dimethylformamide for 4 hours at a temperature in the region of 200° C. The dicyclohexylurea formed is then filtered on a 0.45 µm Millex HV filter (Millipore) and the filter is washed with 0.5 ml of dimethylformamide. 0.972 ml of the filtrate obtained (corresponding to 41 µmol of Fmoc-Arg(Pmc)-Arg(Pmc)-Pro-OH) is then added to 0.5 ml of a solution containing 32 mg (48.6 µmol) of the compound of formula (I) in which R, R' and R" represent methoxy radicals and R'" represents a hydrogen atom and 7 µl (40 µmol) of diisopropylethylamine. The reaction is carried out for 3 hours at a temperature in the region of 20° C. The solvent is then removed by virtue of a Speed Vac (Savant) centrifugal evaporator equipped with a vane pump for 18 hours at a temperature in the region of 20° C. The residue is then taken up in 10 ml of a trifluoroacetic acid/phenol/ethanedithiol/thioanisole/water mixture (40131112/2 by volume) and left to react for 90 minutes at a temperature in the region of 20° C., with stirring. The mixture is then concentrated on an RC10–10 (Jouan) centrifugal evaporator equipped with a vane pump for 45 minutes (temperature of the evaporation chamber 50° C., trapping the vapours at −90° C). 30 ml of a tert-butyl methyl ether/petroleum ether mixture (1/1 by volume) are added to the concentrate obtained (approximately 2 ml) in order to precipitate the peptide. This peptide is collected by centrifuging. It is dissolved in 2 ml of trifluoroacetic acid and the precipitation operation is repeated once. The peptide is dried under reduced pressure (3.5 kPa). The product is finally purified by high performance liquid chromatography on a 100 Å $C_{18}$ column (250×10 mm, Bio-Rad), which is eluted with a gradient from 22 to 47% acetonitrile containing 0.07% of trifluoroacetic acid (by volume) in water containing 0.07% of trifluoroacetic acid (by volume) at a flow rate of 6 ml/minute, over 30 minutes, and then lyophilized. 23.6 mg of the ditrifluoroacetate of the compound of formula (II) in which $R_1$—

$(R_2)_m$—$(R_3)_n$—$(R_4)_p$ represents Fmoc-Arg-Arg-Pro-, R, $R_5$ and $R_6$ represent methoxy radicals and $R_7$ represents a hydrogen atom are thus obtained in the form of a white powder [Mass spectrum on Sciex API III, in ESMS (Electrospray Mass Spectrometry): M/z=1290 (M+H)$^+$, M/z=646 (M+2H)$^{2+}$].

We claim:

1. A purified compound of the formula:

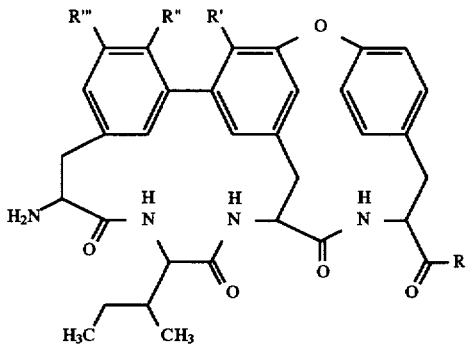

in which R represents a hydroxyl, alkyloxy, phenylalkyloxy or —NH—CH$_2$—COOH radical, R' and R" are identical and each represent a hydroxyl or methoxy radical and R'" represents a hydrogen, bromine, chlorine or iodine atom or a nitro radical, it being understood that the alkyl and alkyloxy radicals and portions contain 1 to 4 carbon atoms in a straight or branched chain, or a salt thereof.

2. A process for the preparation of a compound of formula (I) according to claim 1 in which R, R' and R" represent a hydroxyl radical and R'" represents a hydrogen atom, comprising fermenting A9738 actinomycetes (CBS 162.94), isolating the product and optionally converting the product to a salt thereof.

3. A process for the preparation of a compound of formula (I) according to claim 1 in which R represents a methoxy or phenylalkyloxy radical, comprising esterifying a compound of formula (I) in which R represents a hydroxyl radical, isolating the product and optionally converting the product to a salt thereof.

4. A process for the preparation of a compound of formula (I) according to claim 1 in which R represents an —NH—CH$_2$—COOH radical, comprising reacting a compound of formula (I), in which R represents a hydroxyl radical, with glycine, isolating the product and optionally converting the product to a salt thereof.

5. A process for the preparation of a compound of formula (I) according to claim 1 in which R' and R" represent methoxy radicals, comprising reacting a compound of formula (1), in which R' and R" represent hydroxyl radicals, with trimethylsilyldiazomethane, isolating the product and optionally converting the product to a salt thereof.

6. A process for the preparation of a compound of formula (I) according to claim 1 in which R'" represents a nitro radical, comprising nitrating a compound of formula (I), in which R'" represents a hydrogen atom, isolating the product and optionally converting the product to a salt thereof.

7. A process for the preparation of a compound of formula (I) according to claim 1 in which R'" represents a chlorine atom, comprising chlorinating a compound of formula (I) in which R'" represents a hydrogen atom, isolating the product and optionally converting the product to a salt thereof.

8. A process for the preparation of a compound of formula (I) according to claim 1 in which R'" represents a bromine atom, comprising brominating a compound of formula (I), in which R'" represents a hydrogen atom, isolating the product and optionally converting the product to a salt thereof.

9. A process for the preparation of a compound of formula (I) according to claim 1 in which R'" represents an iodine atom, comprising iodinating a compound of formula (I), in which R'" represents a hydrogen atom, isolating the product and optionally converting the product to a salt thereof.

10. The purified compound according to claim 1, provided that when R is OH, and R'" is hydrogen, then R' and R" are other than a hydroxyl radical.

* * * * *